(12) United States Patent
Kamble et al.

(10) Patent No.: US 12,312,290 B2
(45) Date of Patent: May 27, 2025

(54) ISOBUTYL BENZENE AND A PROCESS FOR SYNTHESIS OF ISOBUTYL BENZENE BY USING A CATALYST

(71) Applicant: MANGALORE REFINERY & PETROCHEMICALS LTD., Mangalore (IN)

(72) Inventors: Sanjay Pandurag Kamble, Pune (IN); Chandrashekhar Vasant Rode, Pune (IN); Nandakumar Velayudhan Pillai, Aluva Ernakulam (IN); Karthick Ramalingam, Abatharanapuram Vadalur (IN); Rohit Ravi Shetty, Kolhapur (IN)

(73) Assignee: MANGALORE REFINERY & PETROCHEMICALS LTD., Mangalore (IN)

( * ) Notice: Subject to any disclaimer, the term of this patent is extended or adjusted under 35 U.S.C. 154(b) by 544 days.

(21) Appl. No.: 17/614,404

(22) PCT Filed: May 28, 2020

(86) PCT No.: PCT/IB2020/055067
§ 371 (c)(1),
(2) Date: Nov. 26, 2021

(87) PCT Pub. No.: WO2020/240460
PCT Pub. Date: Dec. 3, 2020

(65) Prior Publication Data
US 2022/0227686 A1    Jul. 21, 2022

(30) Foreign Application Priority Data
May 31, 2019 (IN) .............................. 201941021772

(51) Int. Cl.
*C07C 2/72* (2006.01)
*B01J 23/02* (2006.01)
(Continued)

(52) U.S. Cl.
CPC ................. *C07C 2/72* (2013.01); *B01J 23/02* (2013.01); *B01J 23/04* (2013.01); *B01J 35/40* (2024.01); *B01J 37/0036* (2013.01)

(58) Field of Classification Search
None
See application file for complete search history.

(56) References Cited

U.S. PATENT DOCUMENTS

| 7,148,177 B2 | 12/2006 | Steinbrenner | |
| 2004/0059168 A1* | 3/2004 | Steinbrenner | C07C 2/72 585/452 |
| 2014/0154160 A1* | 6/2014 | Fisher | B01D 53/94 60/299 |

FOREIGN PATENT DOCUMENTS

| FR | 2703678 A1 | 10/1994 |
| JP | 2018199627 A | * 12/2018 |

OTHER PUBLICATIONS

Machine translation JP 2018-199627. Retrieved Jun. 14, 2024 (Year: 2024).*

(Continued)

*Primary Examiner* — In Suk C Bullock
*Assistant Examiner* — Alyssa L Cepluch
(74) *Attorney, Agent, or Firm* — The Roy Gross Law Firm, LLC; Roy D. Gross

(57) ABSTRACT

The present disclosure provides a process for the synthesis of isobutyl benzene by side chain alkylation of toluene in the presence of a catalyst. The catalyst used in the process of present disclosure provides maximum conversion of toluene with high selectivity towards isobutyl benzene.

6 Claims, 9 Drawing Sheets

(51) Int. Cl.
   *B01J 23/04*  (2006.01)
   *B01J 35/40*  (2024.01)
   *B01J 37/00*  (2006.01)

(56) References Cited

OTHER PUBLICATIONS

Kijenski, J. et al., "Alkylation of Alkyl Aromatic Hydrocarbons over Metal Oxide-Alkali Metal Superbasic Catalysts", Journal of Catalysis, Oct. 25, 2001, vol. 203, Issue No. 2, pp. 407-425.
International Search Report & Written Opinion mailed on Sep. 10, 2020, in PCT Application No. PCT/IB2020/055067 filed on May 28, 2020.

* cited by examiner (a)

(b)

(c)

(a) (b)

200g
ISOBUTYL BENZENE AND A PROCESS FOR SYNTHESIS OF ISOBUTYL BENZENE BY USING A CATALYST

This application is a National Phase of PCT Patent Application No. PCT/IB2020/055067 having International filing date of May 28, 2020, which claims the benefit of priority of Indian Patent Application number 201941021772, filed May 31, 2019, the contents of which are all incorporated herein by reference in their entirety.

FIELD

The present disclosure relates to a process for the synthesis of isobutyl benzene (IBB). Particularly, the present disclosure relates to a process for the synthesis of isobutyl benzene in the presence of a catalyst.

Definitions

As used in the present disclosure, the following terms are generally intended to have the meaning as set forth below, except to the extent that the context in which they are used indicates otherwise.

Ball Mill—A ball mill is a type of grinder used to grind and blend materials for use in mineral dressing processes, paints, pyrotechnics, ceramics and selective laser sintering. It works on the principle of impact and attrition. The size reduction is achieved by impact of dropping balls that fall from near the top of the rotating shell.

Cryo-mill—A cryogenic mill (or cryo-mill) is a type of grinder based on the principle of cryogenic grinding, which includes cooling or chilling a material and then reducing the particle size thereof to obtain a material having a particle size in the desired range, such as in micrometer range or nanometer range.

BACKGROUND

The background information herein below relates to the present disclosure but is not necessarily prior art.

Iso-butyl benzene is a valuable intermediate used in the synthesis of active pharmaceutical intermediates (API). Iso-butyl benzene is used as an intermediate in the synthesis of Ibuprofen, an anti-inflammatory drug. Iso-butyl benzene (IBB) is produced via alkylation of toluene with propylene. The conventional process suffers from drawbacks such as formation of by-products, longer reaction time, low yield and low selectivity for iso-butyl benzene and tedious reaction conditions, etc. In addition, there are difficulties in catalyst handling due to usage of high Na loading. The synthesis of IBB is mainly carried out in a batch mode. It is also observed that the life and stability of the catalyst are limited. Further, it is observed that the catalyst is difficult to recover or recycle and if recovered the amount of recovery is low.

There is, therefore, felt a need for a process for synthesis of iso-butyl benzene (IBB) and a catalyst used in the synthesis of iso-butyl benzene (IBB) which overcomes the above mentioned drawbacks.

OBJECTS

Some of the objects of the present disclosure, which at least one embodiment herein satisfies, are as follows:

An object of the present disclosure is to ameliorate one or more problems of the prior art or to at least provide a useful alternative.

Another object of the present disclosure is to provide a process for the synthesis of iso-butyl benzene.

Still another object of the present disclosure is to provide a selective synthesis of isobutyl benzene using a catalyst.

Yet another object of the present disclosure is to provide a process for preparing the catalyst for the selective synthesis of iso-butyl benzene.

Another object of the present disclosure is to provide a reusable and recyclable catalyst for the synthesis of iso-butyl benzene.

Other objects and advantages of the present disclosure will be more apparent from the following description, which is not intended to limit the scope of the present disclosure.

SUMMARY

The present disclosure provides a process for the selective synthesis of isobutyl benzene via alkylation of toluene with propylene. The process comprises in-situ preparation of a catalyst under vacuum by reacting active metal and support at a temperature in the range of 200° C. to 400° C. in a reactor. The catalyst comprises the active metal doped on the support. The support has a particle size in the range of 15 nm to 30 nm. The reactor is then cooled at a temperature in the range of 25° C. to 40° C. followed by adding a predetermined amount of toluene in the reactor. Further, a predetermined amount of propylene gas is charged in the reactor by maintaining a temperature in the range of 25° C. to 40° C. to obtain a mixture of propylene and toluene. The mixture is heated at a temperature in the range of 130° C. to 190° C., to obtain isobutyl benzene.

The conversion of toluene into isobutyl benzene, using the catalyst, is increased, and the selectivity of isobutyl benzene prepared by using the catalyst is improved.

Further, the present disclosure provides a catalyst comprising at least one active metal and at least one support, wherein the active metal is doped on the support, and the support has a particle size in the range of 15 nm to 30 nm. The catalyst is prepared by in-situ. The support is selected from a metal carbonate support and a metal oxide support; and the active metal is at least one selected from sodium, potassium, barium and magnesium. In one embodiment, the catalyst has an active metal doped on the metal carbonate support and metal oxide support. In an exemplary embodiment, the catalyst is selected from Na/K$_2$O—MgO, Na/K$_2$O—Ba—MgO, Na/K$_2$O—ZrO$_2$, Na/K$_2$O—Ba—Mg—ZrO$_2$, and Na/Cs$_2$CO$_3$.

Further, the present disclosure provides a process for preparing the catalyst that comprises preparing a support having a particle size in the range of 15 nm to 30 nm; and doping at least one active metal on the support by reacting at least one active metal with at least one support at a temperature in the range of 200° C. to 400° C. under vacuum to obtain the catalyst. The support is prepared by using at least one method selected from ball milling and cryo milling.

BRIEF DESCRIPTION OF THE ACCOMPANYING DRAWING

The present disclosure will now described with the help of the accompanying drawing, in which.

Figure 5:
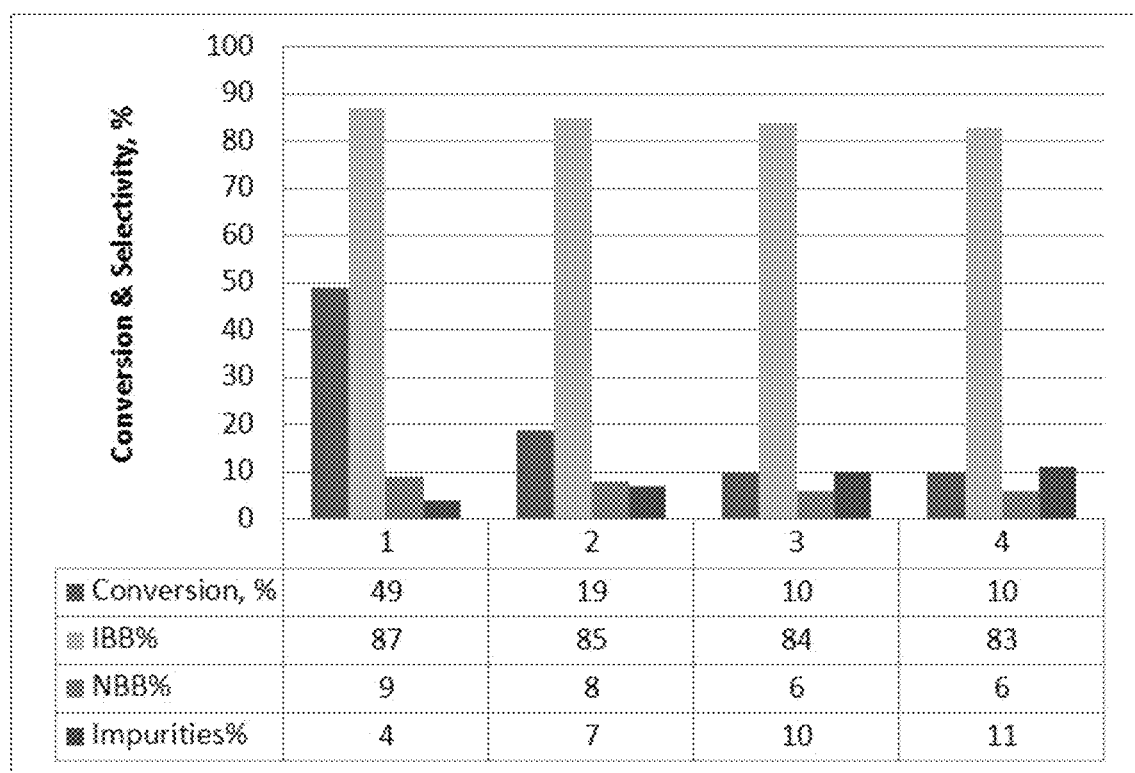
Figure 6:
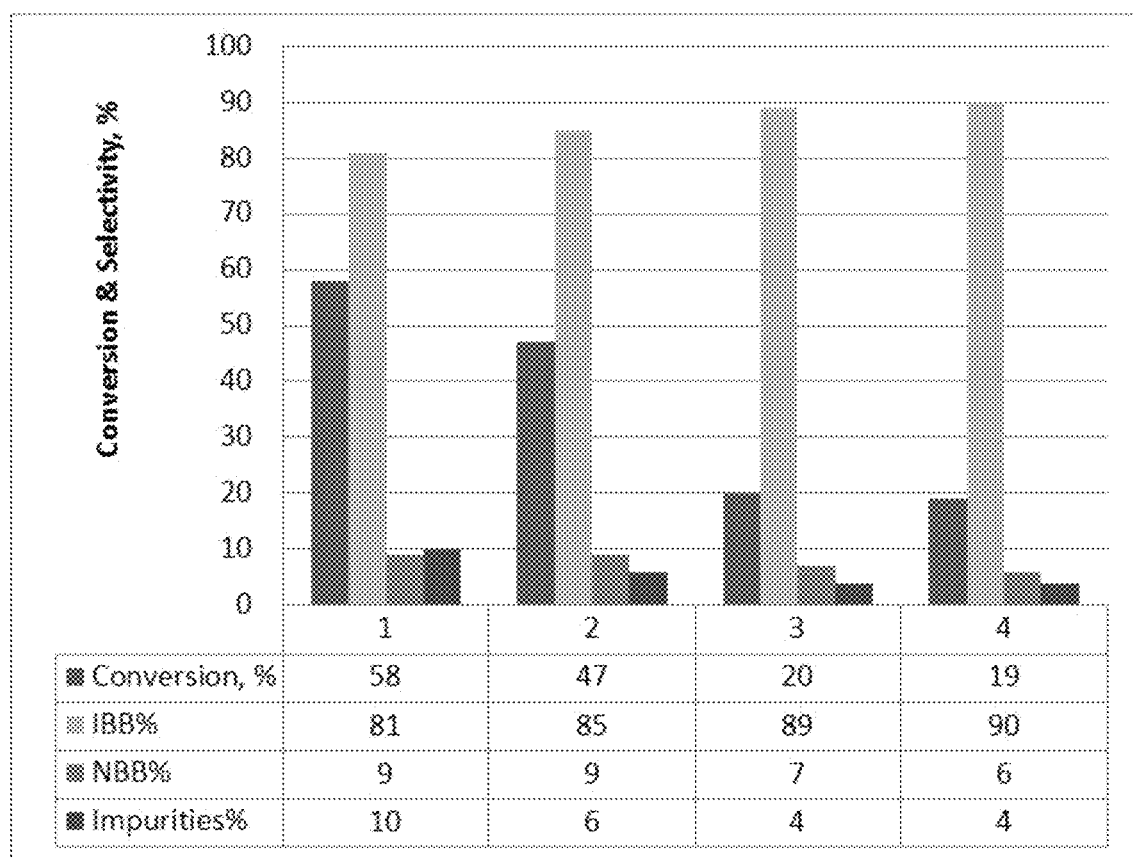

FIG. 5 illustrates a graph on catalyst reusability study and percentage conversion of toluene, IBB selectivity and impurities formed during synthesis of iso-butyl benzene, using the catalyst comprising 15% of sodium doped on potassium carbonate and support prepared in accordance with the present disclosure; and FIG. 6 illustrates a graph of support recycle and percentage conversion of toluene and IBB selectivity using catalyst system comprising 15% sodium doped on potassium carbonate support.

DETAILED DESCRIPTION

Embodiments, of the present disclosure, will now be described with reference to the accompanying drawing.

Embodiments are provided so as to thoroughly and fully convey the scope of the present disclosure to the person skilled in the art. Numerous details are set forth, relating to specific components, and methods, to provide a complete understanding of embodiments of the present disclosure. It will be apparent to the person skilled in the art that the details provided in the embodiments should not be construed to limit the scope of the present disclosure. In some embodiments, well-known processes, well-known apparatus structures, and well-known techniques are not described in detail.

The terminology used, in the present disclosure, is only for the purpose of explaining a particular embodiment and such terminology shall not be considered to limit the scope of the present disclosure. As used in the present disclosure, the forms "a," "an," and "the" may be intended to include the plural forms as well, unless the context clearly suggests otherwise. The terms "comprises," "comprising," "including," and "having," are open ended transitional phrases and therefore specify the presence of stated features, integers, steps, operations, elements, modules, units and/or components, but do not forbid the presence or addition of one or more other features, integers, steps, operations, elements, components, and/or groups thereof. The particular order of steps disclosed in the method and process of the present disclosure is not to be construed as necessarily requiring their performance as described or illustrated. It is also to be understood that additional or alternative steps may be employed.

Iso-butyl benzene is an important drug intermediate that is synthesized by alkylation of toluene using propylene, and employing a conventional catalyst. The conventional catalyst suffers from drawbacks such as low yield, & low selectivity for desired product i.e. isobutyl benzene. Further, the catalyst stability and recyclability is a major concern.

The present disclosure provides a process for the selective synthesis of iso-butyl benzene from toluene and propylene in the presence of a catalyst.

In accordance with a first aspect of the present disclosure, a process for the synthesis of iso-butyl benzene from toluene and propylene, using a catalyst is provided. The reaction is illustrated as follows:

Scheme 1: Synthesis of isobutyl benzene by alkylation of toluene

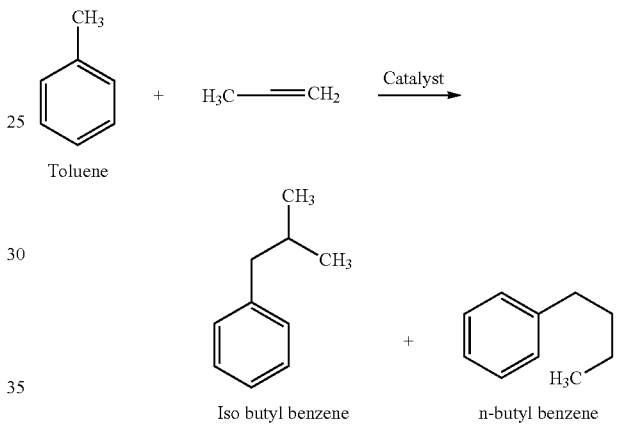

The present disclosure provides a process for the selective synthesis of isobutyl benzene via alkylation of toluene with propylene.

The process comprises in-situ preparation of catalyst under vacuum by reacting active metal and support at a temperature in the range of 200° C. to 400° C. in a reactor. The catalyst comprises an active metal doped on a support. The support has a particle size in the range of 15 nm to 30 nm. The reactor is the cooled to a temperature in the range of 25° C. to 40° C. A pre-determined amount of toluene is introduced in the reactor followed by charging a predetermined amount of propylene gas in the reactor by maintaining the temperature of the reactor in the range of 25° C. to 40° C. to obtain a mixture of propylene and toluene. The mixture is heated at a temperature in the range of 130° C. to 190° C., to obtain isobutyl benzene.

In accordance with the present disclosure, the conversion of toluene, using the catalyst, is in the range of 10% to 75%, and the IBB selectivity is in the range of 75 to 90%.

In another aspect, the present disclosure provides a catalyst and a process for preparation thereof.

The catalyst comprising at least one active metal and at least one support, wherein the active metal is doped on the support, and the support has a particle size in the range of 15 nm to 30 nm. The catalyst is prepared by in-situ. The catalyst has an active metal doped on the metal carbonate support and metal oxide support. The catalyst used in the process of present disclosure provides maximum conversion of toluene with high selectivity towards isobutyl benzene.

The support is selected from a metal carbonate support and a metal oxide support; and the active metal is at least one selected from sodium, potassium, barium and magnesium. In one embodiment, the catalyst has an active metal doped on the metal carbonate support and metal oxide support. In an exemplary embodiment, the catalyst is selected from Na/$K_2O$—MgO, Na/$K_2O$—Ba—MgO, Na/$K_2O$—$ZrO_2$, Na/$K_2O$—Ba—Mg—$ZrO_2$, and Na/$Cs_2CO_3$.

Further, the present disclosure provides a process for preparing the catalyst that comprises preparing a support having a particle size in the range of 15 nm to 30 nm; and doping at least one active metal on the support by reacting at least one active metal with at least one support at a temperature in the range of 200° C. to 400° C. under vacuum to obtain the catalyst. The support is prepared by using at least one method selected from ball milling and cryo milling.

In accordance with the present disclosure, the catalyst is either metal carbonate support having a particle size in the range of 15 nm to 30 nm, or metal oxide support.

An active metal is doped on the metal carbonate support and/or the metal oxide support. In one embodiment, the catalyst comprises at least one support in an amount in the range of 65 wt % to 90 wt % of the total weight of the catalyst, and at least one active metal in an amount in the range of 10 wt % to 35 wt % of the total weight of the catalyst.

The pre-determined weight ratio of catalyst to the toluene is in the range of 1:6 to 1:20.

The active metal is selected from the group consisting of alkali metal and alkaline earth metal.

The active metal is at least one selected from sodium, potassium, barium and magnesium. In one embodiment the active metal is sodium. In another embodiment the active metal is potassium.

The support is selected from a metal carbonate support and a metal oxide support.

The metal carbonate is selected from the group consisting of potassium carbonate ($K_2CO_3$), sodium carbonate ($Na_2CO_3$), cesium carbonate ($Cs_2CO_3$), and rubidium carbonate ($Rb_2CO_3$).

The pre-determined weight ratio of toluene to propylene is in the range of 1:0.5 to 1:20. Typically, the pre-determined weight ratio of toluene to propylene is in the range of 1:0.5 to 1:2.

The metal oxide is at least one selected from potassium oxide ($K_2O$), magnesium oxide (MgO), barium oxide (BaO) and zirconium oxide ($ZrO_2$). In one embodiment, the metal oxide is a combination of potassium oxide, and magnesium oxide. In another embodiment, the metal oxide is a combination of potassium oxide, and barium oxide. In still another embodiment, the metal oxide is a combination of potassium oxide, and zirconium oxide.

Examples of catalyst comprising a combination of metal oxide support and an active component, is selected from potassium oxide-magnesium oxide support ($K_2O$—MgO), potassium oxide-zirconium oxide support ($K_2O$—$ZrO_2$), potassium oxide-barium oxide-magnesium oxide support ($K_2O$—BaO—MgO), potassium oxide-magnesium oxide-zirconium oxide support ($K_2O$—MgO—$ZrO_2$) in insitu catalyst preparation procedure. Another combination of catalyst comprising active metal component, in accordance with the present disclosure, include, but not limited to, sodium doped on potassium oxide magnesium oxide support (Na doped on $K_2O$—MgO), sodium doped on potassium oxide zirconium oxide support (Na– doped on $K_2O$—$ZrO_2$), sodium doped on potassium oxide barium oxide magnesium oxide support (Na doped on $K_2O$—BaO—MgO), and sodium doped on potassium oxide-magnesium oxide-zirconium oxide support (Na doped on $K_2O$ MgO—$ZrO_2$).

In accordance with an embodiment of the present disclosure, the separation of the precipitate is achieved by filtration.

In accordance with an embodiment of the present disclosure, initially catalyst is prepared in-situ under vacuum by reacting active metal and support. A predetermined amount of toluene is charged into a reactor employing a positive displacement pump under vacuum. Positive displacement pump is used to pump definite quantity of liquid at constant flow rate and fixed pressure. Subsequently, propylene is charged into reactor directly from a propylene gas cylinder via propylene mass flow controller to obtain a mixture comprising toluene and propylene. The mixture is thereafter heated at a pre-determined temperature and for a predetermined time period to obtain desired product i.e., iso-butyl benzene. The predetermined temperature is in the range of 130° C. to 190° C. The samples are withdrawn and analyzed for its content by using gas chromatography.

In the present disclosure, the catalyst consisting of Na supported on nano $K_2CO_3$ provides remarkable conversion of toluene up to 65%, and with more than 77% selectivity for iso-butyl benzene. Thus, the catalyst of the present disclosure provides two-fold higher conversion of toluene as compared to bulk $K_2CO_3$.

Figure 1:
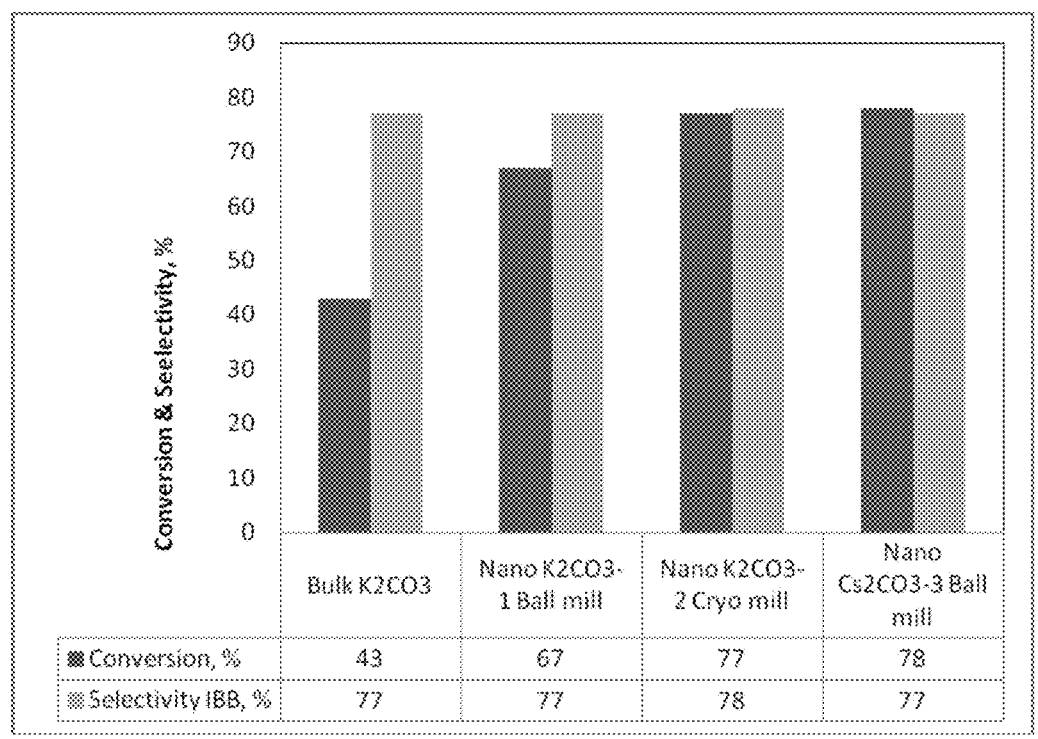
FIG. 1 illustrates a graph of the percentage conversion of toluene and iso-butyl benzene selectivity by using a conventional catalyst and the catalyst in accordance with the present disclosure.

In the present disclosure, reproducibility of the synthesis of isobutyl benzene from toluene and propylene are studied by using same amount of fresh 30% nano Na—$K_2CO_3$ as catalyst, in each batch under same operation conditions. FIG. 1, clearly illustrates that 30% Na doped on bulk $K_2CO_3$ showed 43% conversion of toluene and 77% selectivity for iso-butyl benzene. As evidenced from the catalyst screening, the $K_2CO_3$ acts as a promising support for alkylation of toluene to iso-butyl benzene. The support was modified using cryo-milling or ball milling techniques in order to produce nano $K_2CO_3$. The catalyst consisting of Na doped on nano $K_2CO_3$, (modified support), leads to 67% conversion of toluene with more than 77% selectivity for iso-butyl benzene (FIG. 1, nano $K_2CO_3$ support).

In the present disclosure, of all the catalysts comprising activated metal doped on metal carbonate nano-supports, catalyst consisting of sodium (Na) doped on carbonates ($Cs_2CO_3$) provides the most efficient conversion of toluene, i.e. 78% conversion, along with highest selectivity for iso-butyl benzene, i.e. 77% (FIG. 1).

In the present disclosure, the catalysts comprising activated 15% and 30% Na metal doped on mixed metal oxide (i.e. $K_2O$—BaO—$ZrO_2$ and $K_2O$—MgO—$ZrO_2$), prepared by co-precipitation method were evaluated for the selective synthesis of isobutyl benzene from toluene and propylene.

In the present disclosure, the catalysts consisting of Na doped on mixed metal oxide supports (FIGS. 3 and 4) provided 3 to 9% conversion of toluene and showed 70 to 85% IBB selectivity. Thus, the present disclosure, involves development of mixed metal oxide supports as against metal carbonate supports which have limitations due to their thermal degradation and coke formation.

In the present disclosure, the catalysts consisting of Na doped on mixed metal oxides [i.e. Na/$K_2O$—MgO, Na/$K_2O$—BaO—MgO, Na/$K_2O$—$ZrO_2$, Na/$K_2O$—BaO—MgO—$ZrO_2$, KL-Zeolite, K-Carbon], improve dispersion Na metal and modify the basic strength of catalyst, which leads to improved selectivity for the synthesis of isobutyl benzene from toluene.

In a second aspect, the present disclosure provides a process for the preparation of a catalyst for the synthesis of iso-butyl benzene from toluene and propylene, the process comprises calcining at least one metal carbonate support having a particle size in the range of 5 to 95 nm, at a temperature in the range of 250 to 800° C. to obtain a calcined metal carbonate support. The at least one active metal is doped on the calcined metal carbonate support under vacuum, at a temperature in the range of 200 to 400° C., to obtain the catalyst for the synthesis of iso-butyl benzene from toluene.

In accordance with the present disclosure, the metal carbonate support is a nano-sized support. The metal carbonate is processed to obtain nano-sized particles.

The nano-sized particles of the metal carbonate support are calcined at a temperature in the range of 250 to 800° C. to obtain a calcined metal carbonate support. An active component, which is an active metal, along with a fluid medium is mixed with the calcined metal carbonate support to obtain a mixture thereof. The resultant mixture is continuously stirred and heated under vacuum for a predetermined time period, to obtain the catalyst comprising the active component (active metal) and the support (metal carbonate support).

In accordance with the present disclosure, the calcination temperature is in the range of 200° C. to 500° C., preferably in the range of 250° C. to 400° C., whereas the temperature of heating the mixture comprising active metal component and the metal carbonate support is in the range of 200° C. to 400° C. and the catalyst is prepared under vacuum. The time period for catalyst calcination is in the range of 1 hour to 24 hours, whereas the time period for heating the mixture is in the range of 1 hour to 10 hours, preferably 3 hours to 6 hours.

In one embodiment, the milling of the metal carbonate support is done using a ball mill.

In another embodiment, the milling of the metal carbonate support is carried out using a cryo-mill.

The milled metal carbonate support particles typically have a particle-size of less than 80 nanometer (nm).

In an embodiment, the particle size of the milled nano-sized metal carbonate support particles is in the range of 15 nanometer (nm) to 30 nanometer (nm).

In the present disclosure, it is observed that by using ball milling technique particle size of nano $K_2CO_3$ obtained is in the range of 18 to 29 nm. Whereas, cryo milling of $K_2CO_3$ lead to nano $K_2CO_3$ having particle size in the range of 22 to 28 nm.

More specifically, in an embodiment in accordance with the present disclosure, the metal carbonate support is milled employing the ball mill technique, wherein a predetermined amount of an anhydrous metal carbonate, a fluid medium and an acid are mixed to obtain a mixture thereof. The mixture is introduced into a ball mill reactor and milled at ambient temperature for a predetermined time period to obtain nano-sized particles of the metal carbonate support, wherein the particle size is less than 80 nanometer (nm) and preferably in the range of 15 to 30 nanometer (nm). The fluid medium is an alcohol selected from ethanol, propanol, glycerol mixed with 1% to 5% acid selected from levulinic acid and lactic acid.

Further, in another embodiment in accordance with the present disclosure, the metal carbonate support is milled employing the cryo-milling technique, wherein a predetermined amount of an anhydrous metal carbonate and a fluid medium are mixed to obtain a mixture thereof. The mixture is introduced into a cryo-mill reactor wherein the mixture is milled at a pre-determined temperature, which is cryogenic temperature, for a pre-determined time period and frequency of cryo-cycles. The pre-determined temperature, in an embodiment, is in the range of −150° C. to −250° C., whereas the predetermined time period, in an embodiment, is in the range of 1 minute to 10 minutes. In an embodiment, the cryo-cycles are in the range of 4 to 8 and the cryo-cycles have a frequency of 1 Hertz (Hz) to 25 Hertz (Hz). The particle size is less than 80 nanometer (nm) and preferably in the range of 15 nanometer (nm) to 30 nanometer (nm). The fluid medium is an alcohol such as ethanol, propanol, glycerol etc.

In a third aspect, the present disclosure provides a process for the preparation of a catalyst for the side chain alkylation of toluene, said process comprises mixing at least one aqueous solution of metal salts and an aqueous solution of active metal carbonate to obtain an aqueous mixture. The aqueous mixture is subjected to co-precipitation at a temperature in the range of 25 to 30° C., followed by aging of the precipitate for a time period in the range of 15 to 30 hour, to obtain aqueous slurry comprising a mixed metal oxides support. The active mixed metal oxide support is filtered from the aqueous slurry, and the separated precipitate is dried, under vacuum, at a temperature in the range of 100 to 300° C., to obtain the catalyst support for the side chain alkylation of toluene.

The metal salt is selected from the group consisting of barium nitrate, magnesium nitrate, zirconium sulphate and zirconium nitrate.

The alkali metal carbonate is selected from the group consisting of sodium carbonate, potassium carbonate, cesium carbonate, and rubidium carbonate.

The aqueous solution of the metal salt and the aqueous solution of the active metal carbonate, independently have a concentration in the range of 0.2 M to 1 M.

An aqueous solution of a compound comprising the active metal oxide component is precipitated using a predetermined amount of active metal carbonate, typically alkali or alkaline earth metal carbonates at ambient temperature for a predetermined time period. The precipitate is aged for a predetermined time period. The aged precipitate is separated and then dried at a predetermined temperature for a predetermined time period. In an embodiment, the temperature of drying of the aged precipitate is in the range of 100° C. to 120° C. and the time period is in the range of 1 hour to 5 hours.

In accordance with a fourth aspect of the present disclosure, a process for in-situ preparation of the catalyst and synthesis of iso-butyl benzene is disclosed. Typically, the in-situ preparation of the catalyst and the synthesis of the iso-butyl benzene are carried out in a single reactor.

More specifically, the reaction is carried out in a high pressure autoclave/reactor equipped with a temperature sensor, pressure gauge; vent valve, safety rupture disc, gas inlet-valve, liquid sampling valve, agitator with an impeller having 4 pitched blades, motor, solenoid valve and a sampling port. Reaction pressure, temperature and agitator speed are continuously monitored using the control panel during the course of the reaction. The high-pressure reactor is operated under vacuum, typically of 100 mbar to 230 mbar. Support is loaded into the high-pressure reactor and the active component (metal) is doped on the support under vacuum at a predetermined temperature, typically in the range of 200° C. to 300° C., to obtain the catalyst.

Thereafter, toluene is charged into the high pressure reactor with the help of positive displacement pump under vacuum. Propylene is charged into reactor directly from a propylene gas cylinder via propylene mass flow controller to obtain toluene and propylene gas mixture. The mixture along with catalyst is heated at predetermined temperature, typically in the range of 130° C. to 190° C. The reaction samples are withdrawn and analyzed for its content by using gas chromatography.

The catalyst of the present disclosure is recycled by following process. Typically, after the completion of first reaction, the reaction products is withdrawn from the high pressure reactor and remaining catalyst is washed twice or thrice with alcohol, followed by drying of the metal carbonate support at a temperature in the range of 110° C. to 150° C. for 1 hour to 24 hours and further calcined at a temperature in the range of 200° C. to 400° C. for 3 hours to 6 hours.

The foregoing description of the embodiments has been provided for purposes of illustration and not intended to limit the scope of the present disclosure. Individual components of a particular embodiment are generally not limited to that particular embodiment, but, are interchangeable. Such variations are not to be regarded as a departure from the present disclosure, and all such modifications are considered to be within the scope of the present disclosure.

The present disclosure is further described in light of the following experiments which are set forth for illustration purpose only and not to be construed for limiting the scope of the disclosure. The following experiments can be scaled up to industrial/commercial scale and the results obtained can be extrapolated to industrial scale.

EXPERIMENTAL DETAILS

Experiment 1

Experiment 1A—Preparation of Metal Carbonate Support

Anhydrous alkali metal carbonate, absolute ethanol and levulinic acid (as dispersing agent) were mixed and poured into a ball mill. The mixture was milled to obtain metal carbonate support. The process details are summarized in Table 1.

TABLE 1

PROCESS DETAILS FOR NANO SUPPORT PREPARATION BY BALL MILLING

| S. No. | Alkali metal carbonate (grams) | Fluid medium-Absolute ethanol (ml) | Levulinic Acid (grams) | Milling technique | Milling temperature (° C.) | Milling time (hours) | Support (Particle size in nm) |
|---|---|---|---|---|---|---|---|
| 1 | $K_2CO_3$ (10) | 4.2 | 0.435 | Ball Mill | RT | 8 | Nano-$K_2CO_3$ (18-29 nm) |
| 2 | $Cs_2CO_3$ (10) | 4.2 | 0.435 | Ball Mill | RT | 8 | Nano-$Cs_2CO_3$ (22-27 nm) |

Experiment 1B—Preparation of Metal Carbonate Support

An anhydrous alkali metal carbonate and absolute ethanol were mixed and the mixture so obtained was poured into a Cryo-mill. The mixture was milled to obtain nano alkali metal carbonate support. The process details are summarized in Table 2.

TABLE 2

PROCESS DETAILS FOR NANO SUPPORT PREPARATION BY CRYO MILLING

| S. No | Alkali metal carbonate (grams) | Fluid medium-Absolute ethanol (ml) | Milling technique | Frequency ($sec^{-1}$) | Cryo-cycle | Time for one cycle (minutes) | Frequency in hertz (Hz) & and each for 2.5 minutes | Milling temperature (° C.) | Support (Particle size in nm) |
|---|---|---|---|---|---|---|---|---|---|
| 1 | 5 ($K_2CO_3$) | 2.5 | Cryo mill | 5.0 | 6 | 5 | 5 & 20 | −196 | Nano $K_2CO_3$ 22-28 nm) |

Experiment 2—Process of Doping of an Active Metal on Metal Carbonate Support (Catalyst of the Present Disclosure)

Support obtained in experiment 1A and 1B was calcined, followed by the addition of active metal doped on metal oxides or metal carbonate support. The process details are summarized in Table 3.

TABLE 3

PROCESS DETAILS FOR SYNTHESIS OF CARBONATE SUPPORTED CATALYST

| S. No. | Support | support (grams) | Active Metal | Active Metal (grams) | Calcination temperature (° C.) | Calcination time (hours) | Heating temperature (° C.) | Heating time (hours) | catalyst obtained |
|---|---|---|---|---|---|---|---|---|---|
| 1* | (particle size: 60 nm to 0.3 micron) $K_2CO_3$ | 1.8 | Na | 0.6 | 300 | 15 | 250 | 5 | Na—$K_2CO_3$ |
| 2 | (particle size: 22-28 nm)Nano $K_2CO_3$ (Ball milling) | 1.8 | Na | 0.6 | 300 | 15 | 250 | 5 | Nano Na—$K_2CO_3$ |
| 5* | (particle size: 15-29 nm) $Cs_2CO_3$ | 1.8 | Na | 0.6 | 300 | 15 | 250 | 5 | Na—$Cs_2CO_3$ |
| 6 | (particle size: 14-15 nm) Nano $Cs_2CO_3$ (Ball milling) | 1.8 | Na | 0.6 | 300 | 15 | 250 | 5 | Nano Na—$Cs_2CO_3$ |
| 9* | (particle size: 53-74 nm) $Na_2CO_3$ | 1.8 | Na | 0.6 | 300 | 15 | 250 | 5 | Na—$Na_2CO_3$ |
| 10 | (particle size: 11-15 nm) Nano-$Na_2CO_3$ (Ball milling) | 1.8 | Na | 0.6 | 300 | 15 | 250 | 5 | Nano Na—$Na_2CO_3$ |

*Control experiment (conventional bulk support)

Experiment 3—Preparation of Metal Oxide Supported Catalyst

Aqueous solution of metal salts were precipitated with aqueous alkali metal carbonate at a room temperature (24° C.) to obtain precipitate of metal oxides support. The precipitate was aged followed by separation of the precipitate by filtration without washing, followed by drying in oven using static air to obtain active mixed metal oxide support.

The process details are summarized in Table 4.

TABLE 4

PROCESS DETAILS FOR SYNTHESIS OF MIXED METAL OXIDE SUPPORTED CATALYST

| S. No. | Metal salts (moles) | Alkali metal carbonate (moles) | Aging time (hours) | Aging temperature (° C.) | Drying temperature (° C.) | Drying time (hours) | Metal oxide supported catalyst obtained |
|---|---|---|---|---|---|---|---|
| 1 | 0.5 $Mg(NO_3)_2$ | 0.5 $K_2CO_3$ | 24 | RT | 110 | 3 | (particle size: 20-32 nm) $K_2O$—MgO |
| 2 | 0.5 $Zr(SO_4)_2$ | 0.5 $K_2CO_3$ | 24 | RT | 110 | 3 | (particle size: 20-32 nm) $K_2O$—$ZrO_2$ |
| 3 | 0.5 $Ba(NO_3)_2$ & $Mg(NO_3)_2$ | 0.5 $K_2CO_3$ | 24 | RT | 110 | 3 | (particle size: 24-48 nm) $K_2O$—BaO—MgO |

Experiment 4—Synthesis of Isobutyl Benzene

Initially in-situ catalyst was prepared in the high pressure reactor and subsequently toluene was charged into the high pressure reactor with the help of positive displacement pump under vacuum at 30° C. Further, propylene was charged into the reactor directly from the propylene gas cylinder via propylene mass flow controller (30° C.). The mixture was heated at desired temperature to obtain isobutyl benzene. The reaction samples were withdrawn and analyzed for its content by using gas chromatography. The process details are summarized in Table 5. It was observed that the Na metal doped $K_2CO_3$ (bulk support) catalyst gave remarkable conversion of toluene in the range of 43% with more than 77% selectivity to IBB. As evidenced from the catalyst screening, the $K_2CO_3$ acts as a promising support for alkylation of toluene to IBB. Therefore, $K_2CO_3$ support was modified using cryo milling and/or ball milling techniques in order to produce nano-$K_2CO_3$. The Na doped on nano $K_2CO_3$, gave 77% conversion of toluene with 78% IBB selectivity. New batches of Na doped on $K_2O$ with metal oxide supports showed high selectivity to IBB about 80% with toluene conversion is in the range of 8-9%.

TABLE 5

PROCESS DETAILS FOR SYNTHESIS OF ISOBUTYL BENZENE

| S. No. | Toluene (grams) | Propylene (grams) | Catalyst used | catalyst (grams) | Reaction temperature (° C.) | Reaction time (hours) | Conversion, % | Selectivity (IBB), % |
|---|---|---|---|---|---|---|---|---|
| 1* | 20 | 18 | Bulk-$K_2CO_3$ | 2 | 190 | 7 | 43 | 77 |
| 2 | 20 | 18 | Nano $K_2CO_3$ (Δ) | 2 | 190 | 7 | 67 | 77 |
| 3 | 20 | 18 | Nano $K_2CO_3$ (Φ) | 2 | 190 | 7 | 77 | 78 |
| 4 | 20 | 18 | Nano $Cs_2CO_3$ (Δ) | 2 | 190 | 7 | 78 | 77 |
| 5 | 20 | 18 | Na—$K_2O$—$ZrO_2$ | 2 | 190 | 7 | 8 | 80 |
| 6 | 20 | 18 | Na—$K_2O$—MgO | 2 | 190 | 7 | 9 | 86 |

*Bulk catalyst (conventional)
Δ—Obtained by ball milling
Φ—Obtained by cryo milling Experiment 5—Synthesis of Isobutyl Benzene by Using In-Situ Prepartation of Supported Catalyst a) The reaction was carried out high pressure autoclave equipped with a temperature sensor, pressure gauge, vent valve, safety rupture disc, gas inlet-valve, liquid sampling valve, and agitator with 1 impeller having 4 pitched blades, motor, solenoid valve and a sampling port. Reaction pressure, temperature and agitator speed were continuously monitored using the control panel during the course of reaction. The high-pressure reactor was flushed with nitrogen at the pressure of 4 kg/cm² to create the inert atmosphere inside the reactor.

a) Support (prepared in experiment 1A or 1B) was loaded into the high-pressure reactor and metals such as Na/Cs/Ru/Ba/Mg was doped on the support under vacuum at 250° C. to obtain a supported catalyst.

b) Toluene was charged into the high pressure reactor with the help of positive displacement pump under vacuum. Propylene was charged into reactor directly from the propylene gas cylinder via propylene mass flow controller. The mixture was heated at desired temperature.

The reaction samples were withdrawn and analyzed for its content by using gas chromatography. After completion of the reaction the conversion of toluene and selectivity isobutyl benzene was found 65% and 80% respectively. The process details are summarized in Table 6.

TABLE 6

PROCESS DETAILS FOR SYNTHESIS OF ISOBUTYL BENZENE USING IN-SITU PREPARED CATALYST

| Sr. No | Autoclave capacity | Toluene (gm) | Propylene (gm) | Reaction Temperature(° C.) |
|---|---|---|---|---|
| 1 | 50 | 20 | 18 | 190 |
| 2 | 500 | 100 | 43 | 190 |

Further, the results obtained in various experiments described herein above are depicted in form of graphs and images in FIGS. 1 to 7.

FIG. 1 illustrates a graph of the percentage conversion of toluene and IBB selectivity using the conventional catalyst and the catalyst in accordance with the present disclosure; As evidenced from the catalyst screening, the $K_2CO_3$ acts as a promising support for alkylation of toluene to IBB. Hence, nano $K_2CO_3$ support was prepared by using cryo-milling or ball milling techniques. This modified catalyst gave 67% to 77% conversion of toluene with 77% IBB selectivity.

Figure 2A:
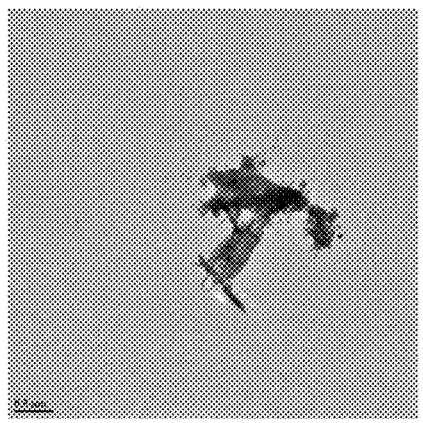
FIG. 2A illustrates high-resolution transmission electron microscopy (HRTEM) images of different supports (a) Bulk $K_2CO_3$—conventional, (b) Nano $K_2CO_3$ (Ball-milled), and (c) Nano $K_2CO_3$(Cryo-milled), prepared in accordance with the present disclosure.
Figure 2A:
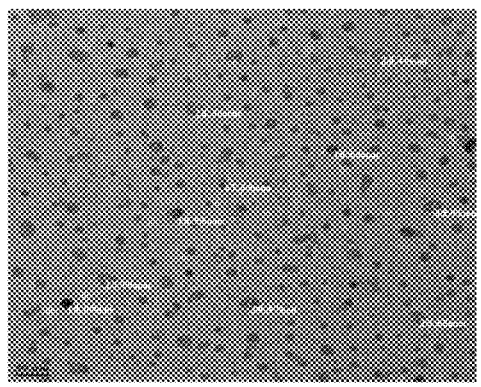
Figure 2A:
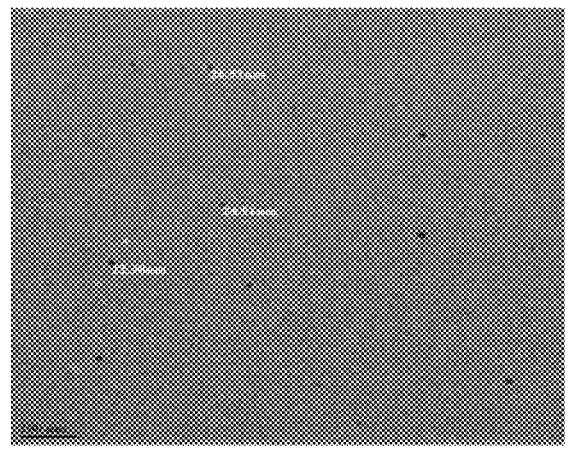

FIG. 2A illustrates high-resolution transmission electron microscopy (HRTEM) images of different supports (a) Bulk $K_2CO_3$—conventional, (b) Nano $K_2CO_3$ (Ball-milled), and (c) Nano $K_2CO_3$(Cryo-milled), prepared in accordance with the present disclosure.

Figure 2B:
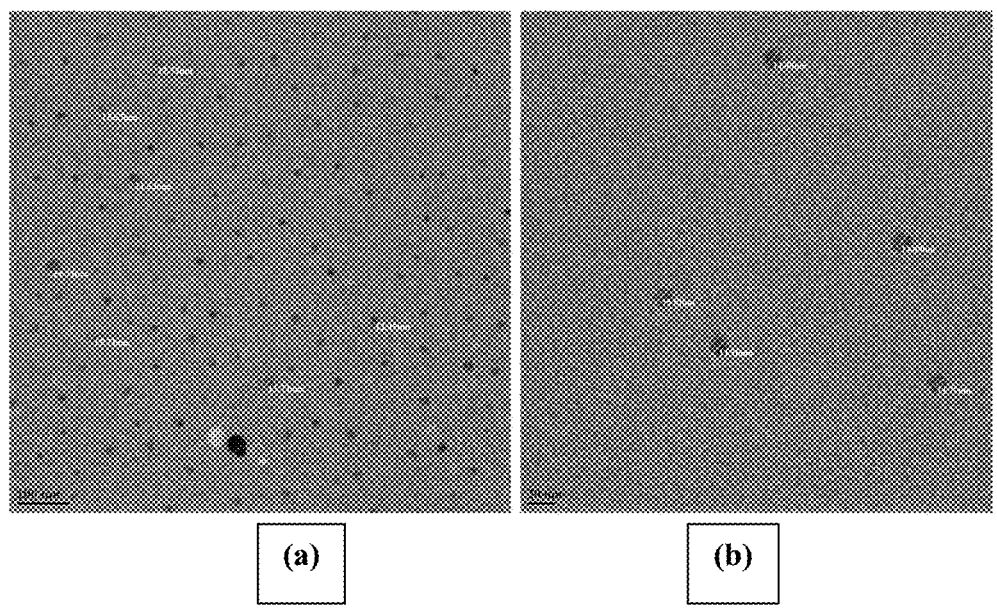
FIG. 2B illustrates high-resolution transmission electron microscopy (HRTEM) images of different supports (a) Bulk $Cs_2CO_3$—conventional, (b) Nano $Cs_2CO_3$ (Ball-milling), prepared in accordance with the present disclosure.

FIG. 2B illustrates high-resolution transmission electron microscopy (HRTEM) images of different supports (a) Bulk $Cs_2CO_3$—conventional, (b) Nano $Cs_2CO_3$ (Ball-milling), prepared in accordance with the present disclosure.

Figure 2C:
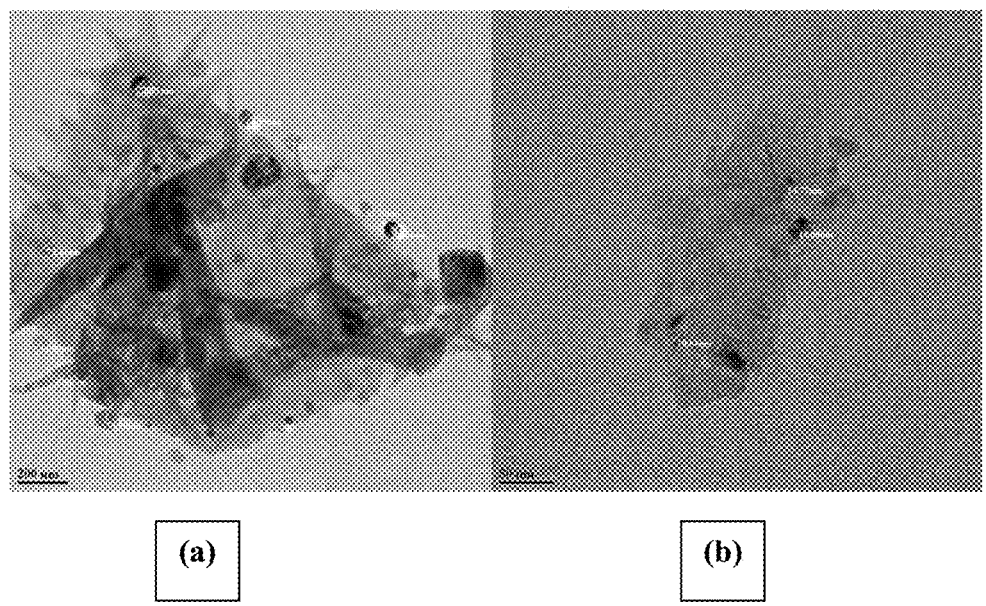
FIG. 2C illustrates high-resolution transmission electron microscopy (HRTEM) images of different supports (a) Bulk $Na_2CO_3$—conventional, (b) Nano $Na_2CO_3$ (Ball-milling), prepared in accordance with the present disclosure.

FIG. 2C illustrates high-resolution transmission electron microscopy (HRTEM) images of different supports (a) Bulk $Na_2CO_3$— conventional, (b) Nano $Na_2CO_3$ (Ball-milling), prepared in accordance with the present disclosure.

Figure 2D:
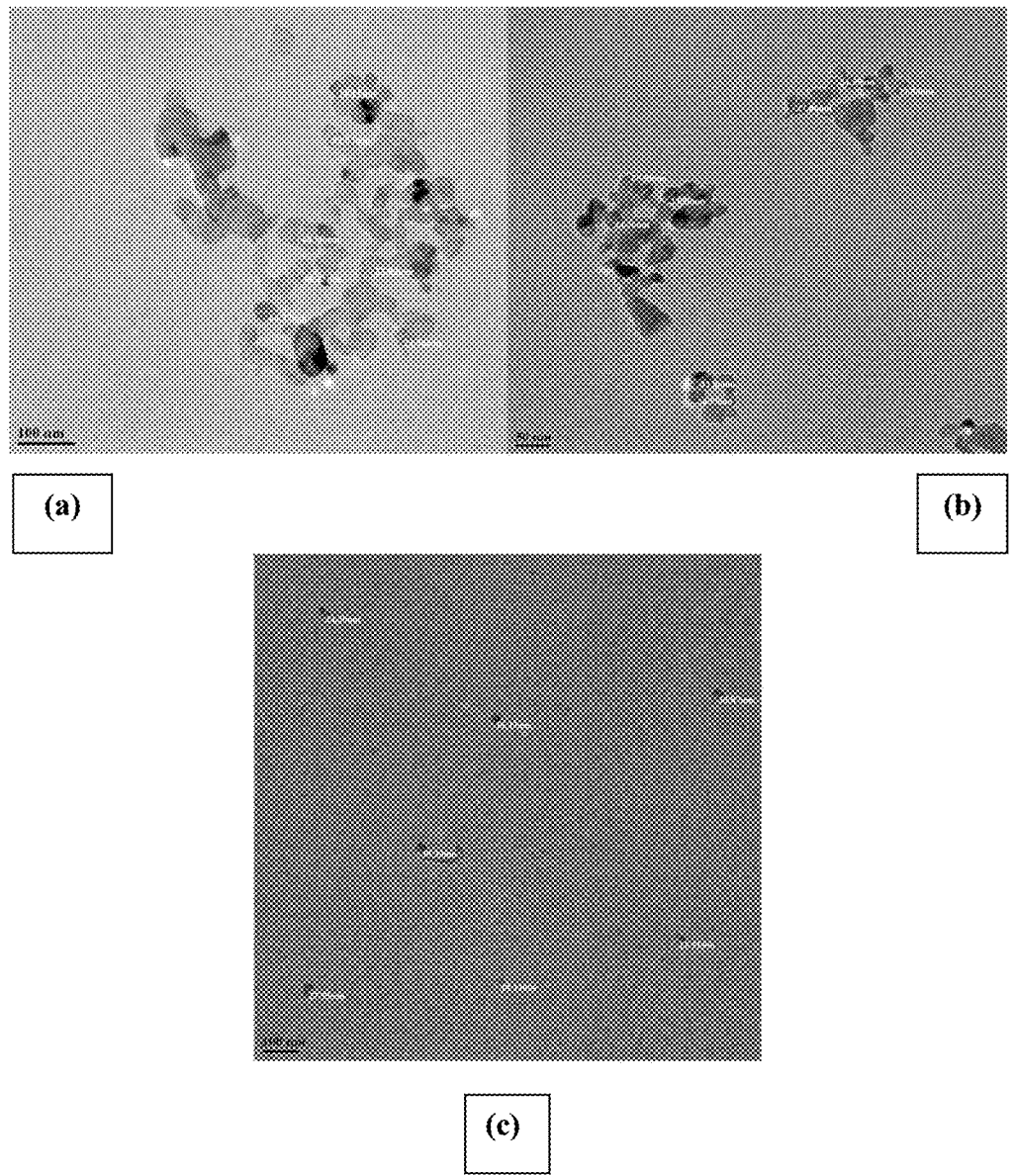
FIG. 2D illustrates high-resolution transmission electron microscopy (HRTEM) images of different supports (a) $K_2O$—BaO, (b) $K_2O$—MgO, and (c) $K_2O$—$ZrO_2$, prepared in accordance with the present disclosure.

FIG. 2D illustrates high-resolution transmission electron microscopy (HRTEM) images of different supports (a) $K_2O$—BaO, (b) $K_2O$—MgO, and (c) $K_2O$—$ZrO_2$, prepared in accordance with the present disclosure.

The HRTEM results showed that, the nano $K_2CO_3$ particle size (18-33 nm) was obtained using milling technique, however bulk $K_2CO_3$ having particle size in the range of 60 nm to 0.3 micron. $Cs_2CO_3$, carbonate support was explored for alkylation of toluene reaction which shows greater than 8% toluene conversion and 77% IBB Selectivity. As evidenced from TEM study, the nano potassium carbonate and cesium carbonate support shows high conversion of toluene with high IBB selectivity. Although, all other mixed oxide support (potassium oxide with metal oxides (MgO, $ZrO_2$ and BaO) shows smaller particle sizes (10-30 nm) with 3-9% toluene conversion and more than 80% selectivity for IBB.

Figure 3:
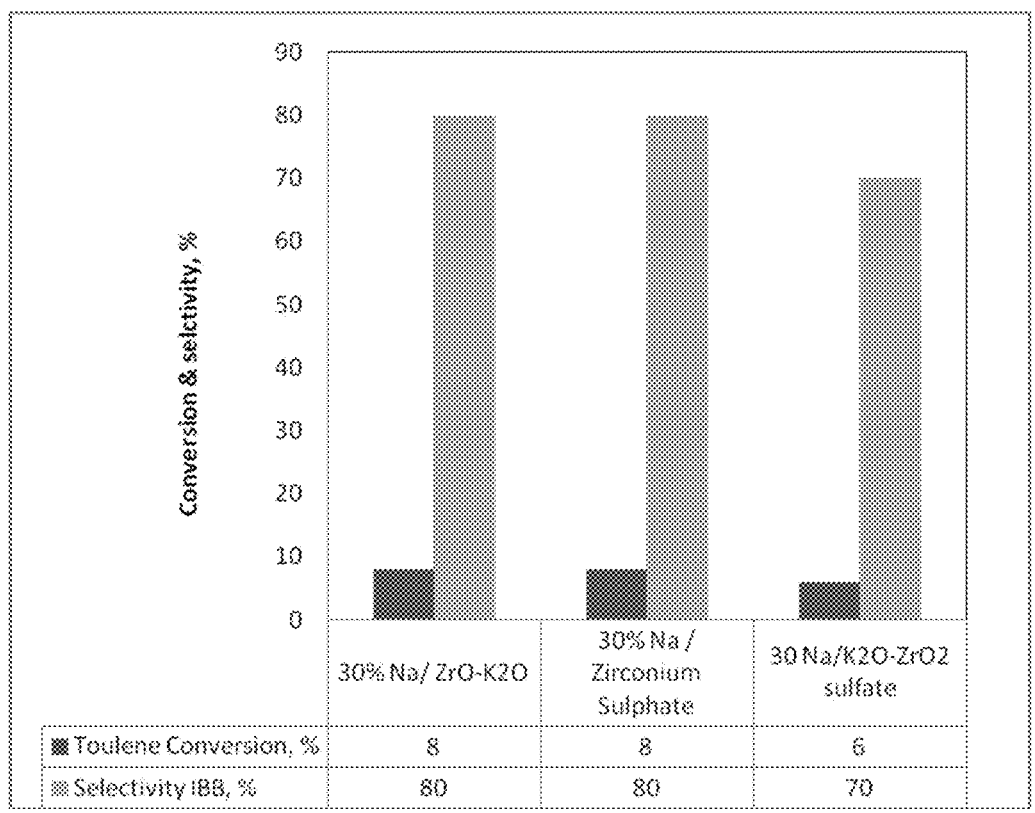
FIG. 3 illustrates a graph of percentage conversion of toluene and IBB selectivity of the catalyst comprising a mixed metal oxides support doped with 30% sodium prepared in accordance with the present disclosure.

FIG. 3 illustrates a graph of percentage conversion of toluene and IBB selectivity of the catalyst comprising a mixed oxides support doped with 30% sodium prepared in accordance with the present disclosure.

Na doped on mixed metal oxide support (potassium oxide zirconium oxide) gives toluene conversion in the range of 6-8% and IBB selectivity in the range of 70-80%.

Figure 4:
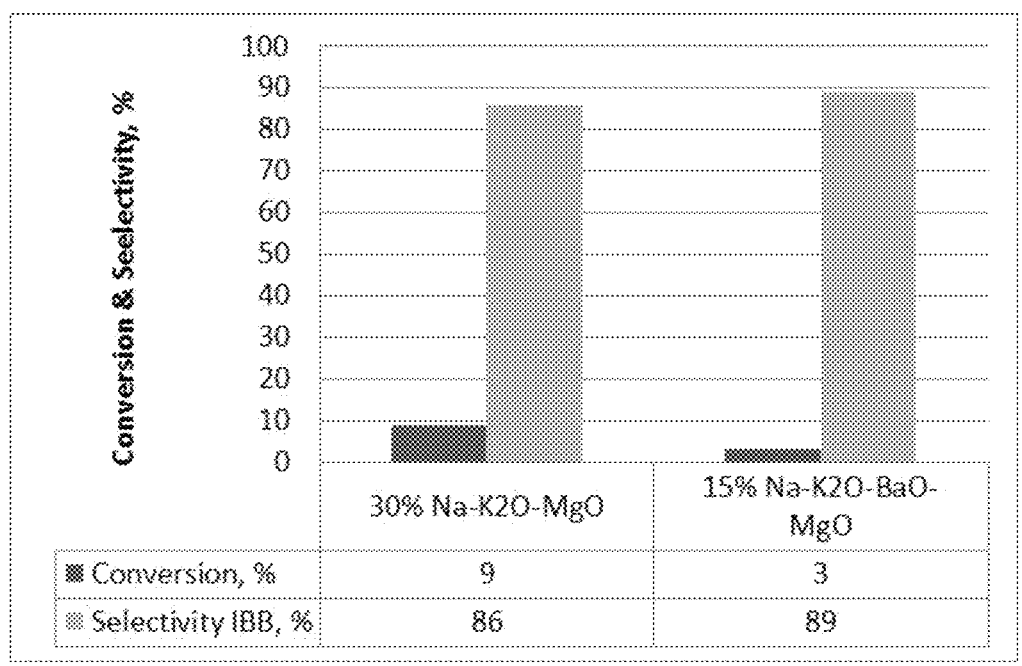
FIG. 4 illustrates a graph of percentage conversion of toluene and IBB selectivity using catalyst system comprising 30% and 15% sodium doped on mixed metal oxide (potassium oxide-magnesium oxide support and potassium oxide-barium oxide-magnesium oxide support), in accordance with the present disclosure.

FIG. 4 illustrates a graph of percentage conversion of toluene and IBB selectivity using catalyst system comprising 30% and 15% sodium doped on mixed oxide (potassium oxide—magnesium oxide support and potassium oxide-barium oxide-magnesium oxide support), in accordance with the present disclosure.

Na doped on mixed metal oxide (30% Na—$K_2O$—MgO and 20% Na—$K_2O$—BaO—MgO) support shows the conversion of toluene 3%, 9% and IBB selectivity 86%, 89% respectively.

FIG. 5 illustrates a graph on catalyst reusability study and percentage conversion of toluene, IBB selectivity and impurities formed during synthesis of iso-butyl benzene, using the catalyst comprising a 15% of sodium doped on potassium carbonate and support prepared in accordance with the present disclosure;

The catalyst reusability study was carried out using 15% Na/K$_2$CO$_3$ catalyst. Initially, fresh 15% Na/K$_2$CO$_3$ shows 49% conversion of toluene with 86% IBB selectivity. The catalyst was reused three times without any pre-treatment shows toluene conversion in the range of 19 to 10% with IBB selectivity in the range of 85 to 83%.

FIG. 6 illustrates a graph of support recycle and percentage conversion of toluene and IBB selectivity using catalyst system comprising 15% sodium doped on potassium carbonate support.

The solid (K$_2$CO$_3$) obtained after the reuse was calcined for 300° C. at 3 h and subsequently used it for the next recycle. This study confirms that, the successive recycle of support using predetermined methodology given in the present disclosure. The toluene conversion dropped from 58% to 20% but the selectivity of IBB was optimum in the range of 80% to 90% with impurities formation in the range of 4% to 10%.

TECHNICAL ADVANCEMENTS

The present disclosure described herein above has several technical advantages including, but not limited to, the realization of the process for synthesis of isobutyl benzene, wherein the process exhibits:

efficient conversion of toluene;
high selectivity for isobutyl benzene; and
catalyst and support reusability and recyclability.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The use of the expression "at least" or "at least one" suggests the use of one or more elements or ingredients or quantities, as the use may be in the embodiment of the invention to achieve one or more of the desired objects or results. While certain embodiments of the inventions have been described, these embodiments have been presented by way of example only, and are not intended to limit the scope of the inventions. Variations or modifications to the formulation of this invention, within the scope of the invention, may occur to those skilled in the art upon reviewing the disclosure herein. Such variations or modifications are well within the spirit of this invention.

The numerical values given for various physical parameters, dimensions and quantities are only approximate values and it is envisaged that the values higher than the numerical value assigned to the physical parameters, dimensions and quantities fall within the scope of the invention unless there is a statement in the specification to the contrary.

While considerable emphasis has been placed herein on the specific features of the preferred embodiment, it will be appreciated that many additional features can be added and that many changes can be made in the preferred embodiment without departing from the principles of the disclosure. These and other changes in the preferred embodiment of the disclosure will be apparent to those skilled in the art from the disclosure herein, whereby it is to be distinctly understood that the foregoing descriptive matter is to be interpreted merely as illustrative of the disclosure and not as a limitation.

The invention claimed is:

1. A process for the synthesis of isobutyl benzene, said process comprising the following steps:
   a) preparing a catalyst by reacting active metal and support, in-situ, under vacuum at a temperature in a range of 200° C. to 400° C. in a reactor, wherein said catalyst comprises an active metal doped on a support, wherein said support is a metal carbonate support which is at least one selected from the group consisting of potassium carbonate (K$_2$CO$_3$), sodium carbonate (Na$_2$CO$_3$), cesium carbonate (CS$_2$CO$_3$), and rubidium carbonate (Rb$_2$CO$_3$), and wherein said support has a particle size in a range of 15 nm to 30 nm;
   b) cooling said reactor at a temperature in a range of 25° C. to 40° C. and introducing a predetermined amount of toluene in said reactor;
   c) charging a predetermined amount of propylene gas in said reactor by maintaining a temperature in a range of 25° C. to 40° C. to obtain a propylene toluene mixture; and
   d) heating said mixture at a temperature in a range of 130° C. to 190° C., to obtain isobutyl benzene.

2. The process as claimed in claim 1, wherein said active metal is at least one selected from sodium, potassium, barium and magnesium.

3. The process as claimed in claim 1, wherein a predetermined weight ratio of the catalyst to toluene is in a range of 1:6 to 1:20.

4. The process as claimed in claim 1, wherein a predetermined weight ratio of toluene to propylene is in a range of 1:0.5 to 1:2.

5. The process as claimed in claim 1, wherein said catalyst is selected from Na/K$_2$CO$_3$ and Na/Cs$_2$CO$_3$.

6. The process as claimed in claim 1, wherein said support is prepared by using at least one method selected from ball milling and cryo milling.

* * * * *